(12) United States Patent
Buys

(10) Patent No.: US 11,307,008 B2
(45) Date of Patent: Apr. 19, 2022

(54) DART AND DART RETAINER

(71) Applicant: Security Devices International (SDI), Wakefield, MA (US)

(72) Inventor: André Johann Buys, Pretoria (ZA)

(73) Assignee: Byrna Technologies Inc., Wakefield, MA (US)

( * ) Notice: Subject to any disclaimer, the term of this patent is extended or adjusted under 35 U.S.C. 154(b) by 231 days.

(21) Appl. No.: 15/775,564

(22) PCT Filed: Nov. 11, 2016

(86) PCT No.: PCT/IB2016/056791
§ 371 (c)(1),
(2) Date: May 11, 2018

(87) PCT Pub. No.: WO2017/081643
PCT Pub. Date: May 18, 2017

(65) Prior Publication Data
US 2018/0328701 A1    Nov. 15, 2018

(30) Foreign Application Priority Data
Nov. 11, 2015    (ZA) .................... 2015/08331

(51) Int. Cl.
*F42B 12/54*    (2006.01)
*A61D 7/00*    (2006.01)
*A61M 5/32*    (2006.01)
*A61M 5/20*    (2006.01)

(52) U.S. Cl.
CPC ............ *F42B 12/54* (2013.01); *A61D 7/00* (2013.01); *A61M 5/329* (2013.01); *A61M 5/3286* (2013.01); *A61M 5/2046* (2013.01); *A61M 2005/206* (2013.01);
(Continued)

(58) Field of Classification Search
CPC ........ F42B 12/54; F42B 12/36; F42B 12/362; F42B 12/46; A61M 5/3286; A61M 5/3287; A61M 5/329; A61M 2005/2013; A61M 2005/206; A61M 2005/3289; A61M 5/158; A61M 5/2046; A61M 5/32; A61M 2005/1586; A61M 2250/00; A61D 7/00
See application file for complete search history.

(56) References Cited

U.S. PATENT DOCUMENTS

| 2,854,925 A | * | 10/1958 | Crockford et al. ..... F42B 12/54 102/512 |
| 3,093,077 A | * | 6/1963 | Harris ..................... F42B 12/54 102/512 |
| 3,207,157 A | | 9/1965 | Murdoch |

(Continued)

FOREIGN PATENT DOCUMENTS

GB    1 450 8530    9/1976

*Primary Examiner* — Shefali D Patel
(74) *Attorney, Agent, or Firm* — Blank Rome LLP

(57) ABSTRACT

The invention relates to a dart (10) comprising a body, the body defining a chamber (24) having a plunger located therein to operatively deliver a substance through a hypodermic needle (32) extending through a front end of the body, and a retainer comprising a barb body locatable on the hypodermic needle (32) characterised in that the barb body is threaded. The invention further relates to a dart retainer, wherein the retainer comprises of a threaded barb body locatable on a hypodermic needle (32) of a dart (10).

7 Claims, 4 Drawing Sheets

Figure 1:
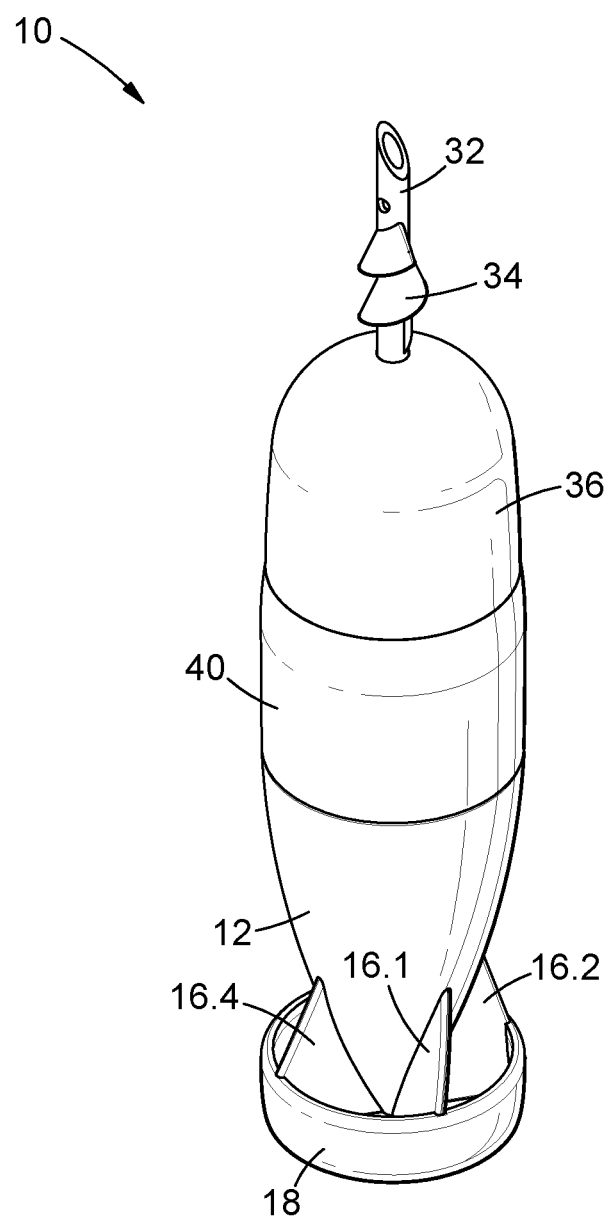

(52) U.S. Cl.
CPC .............. *A61M 2005/2013* (2013.01); *A61M 2005/3289* (2013.01); *A61M 2250/00* (2013.01)

(56) References Cited

U.S. PATENT DOCUMENTS

| | | | | |
|---|---|---|---|---|
| 3,209,695 | A | * | 10/1965 | Crockford ............... F42B 12/54 102/512 |
| 4,863,428 | A | * | 9/1989 | Chevalier ............... F42B 12/54 604/130 |
| 4,884,572 | A | * | 12/1989 | Bays .................. A61B 17/0469 606/139 |
| 5,202,533 | A | | 4/1993 | Vandersteen |
| 8,074,573 | B1 | | 12/2011 | Linker |
| 2009/0013892 | A1 | * | 1/2009 | Judson .................... F42B 10/26 102/502 |
| 2009/0187194 | A1 | * | 7/2009 | Hamada ............. A61B 17/8897 606/104 |
| 2011/0196299 | A1 | * | 8/2011 | Kim ...................... A61M 5/329 604/112 |

\* cited by examiner

DART AND DART RETAINER

CROSS-REFERENCE TO RELATED APPLICATIONS

The present application is the United States national stage of International Patent Application PCT/IB2016/056791, filed Nov. 11, 2016. The present application claims priority to South Africa Patent Application 2015/08331, filed Nov. 11, 2015.

FIELD OF THE INVENTION

This invention relates to non-lethal injection darts and/or injection marking darts and more particularly, but not exclusively, to a dart retainer disposed on the hypodermic needle and a dart incorporating said retainer.

BACKGROUND TO THE INVENTION

Injection darts are frequently required for subcutaneous injection of substances, such as tranquilizers and medicinal substances, into animals. These darts may further include a combination of any of said substances and marking substances.

Darts used in these applications typically comprise a syringe or drug containing chamber terminating in a hypodermic needle which operatively penetrates the skin of the animal. The impact of the dart causes the substance to be delivered subcutaneously to the animal, or the dart may include an ignition system which detonates on impact to facilitate delivery of the substance into the animal.

To allow sufficient time for proper and complete delivery of the substance, the darts are often configured to be retained on the animal. The darts are also retained on the animal so that the dart may be retrieved by a user and reused at a later stage as some of these darts are fairly expensive.

To retain the dart on the animal, the hypodermic needles of these typical darts include barbed collars of a suitable polymer or wire barbs. These prevent or at least minimise the incidence of the dart falling off the animal and retains the dart on the animal until it can be removed by the user. The barbed collars are usually annular and tapers outwardly towards the operatively back end of the barb to form a lip which causes the dart to be retained on the animal.

A disadvantage of these dart retainers is that they cause tissue damage to the animal when the dart is removed from the animal.

A further disadvantage of the barbed collars is that the collars often slide off the needle and stay behind in the animal as the needle is withdrawn resulting in a foreign and often undesired object remaining subcutaneously. In this case, the retaining means will also have to be replaced on the needle resulting in higher costs.

A yet further disadvantage of known darts are that they are required to be fired from specialised and fairly expensive weapons intended specifically and exclusively for firing the mentioned darts.

OBJECT OF THE INVENTION

It is accordingly an object of the current invention to provide a dart retainer and a dart incorporating same with which the abovementioned disadvantages could at least partially be alleviated or overcome.

SUMMARY OF THE INVENTION

According to a first aspect of the invention, there is provided a dart comprising a body, the body defining a chamber having a plunger located therein to operatively deliver a substance through a hypodermic needle extending through a front end of the body, and a retainer comprising a barb body locatable on the hypodermic needle characterised in that the barb body is threaded.

According to the invention the body includes a stabilising member connected thereto for stabilising the projectile in flight when the projectile is discharged from a weapon, and an annular member connected to the stabilising member at a rear end of the dart.

The invention further provides for the chamber to include a striker pin configured to operatively strike a primer for actuating the plunger to deliver the substance.

The striker pin, primer and plunger may be disposed in an insert.

The invention yet further provides for the front end of the body to include a shock absorber member.

Further according to the invention, the annular member may have substantially the same circumference as the front end of the body.

Further according to the invention, the circumference of the body decreases towards the annular member and the stabilising member may be a plurality of fins helically arranged relative to the body to cause the dart to operatively spin along its longitudinal axis; and wherein the orientation of the helices of the fins and barb body is the same.

The invention further provides for the annular member to include rifling lands and grooves.

According to a second aspect of the invention, there is provided a dart retainer comprising a barb body locatable on a hypodermic needle of a dart characterised in that the body is threaded.

The invention further provides for the dart retainer to be manufactured from a water soluble material.

According to a third aspect of the invention there is provided for a hypodermic needle for a dart having a dart retainer located thereon, the dart retainer having a barb body characterised in that the body is threaded.

BRIEF DESCRIPTION OF THE ACCOMPANYING DIAGRAMS

Figure 2:
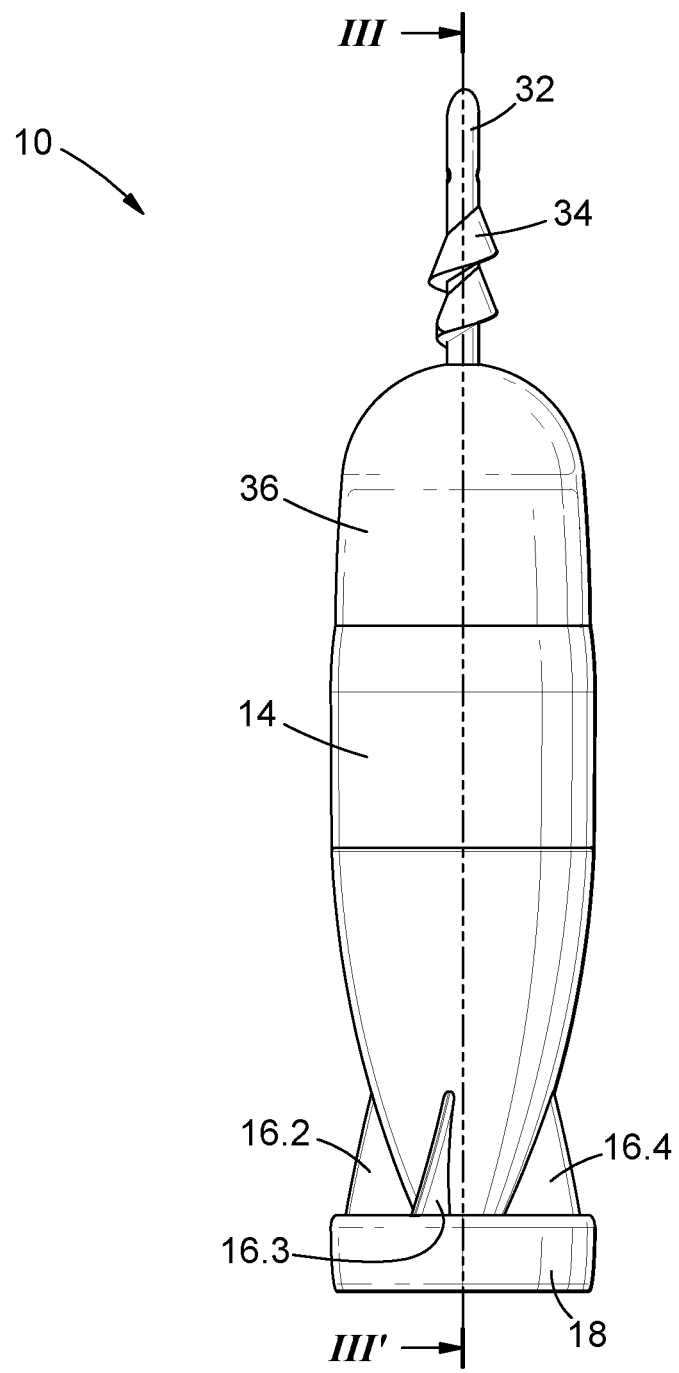
Figure 3:
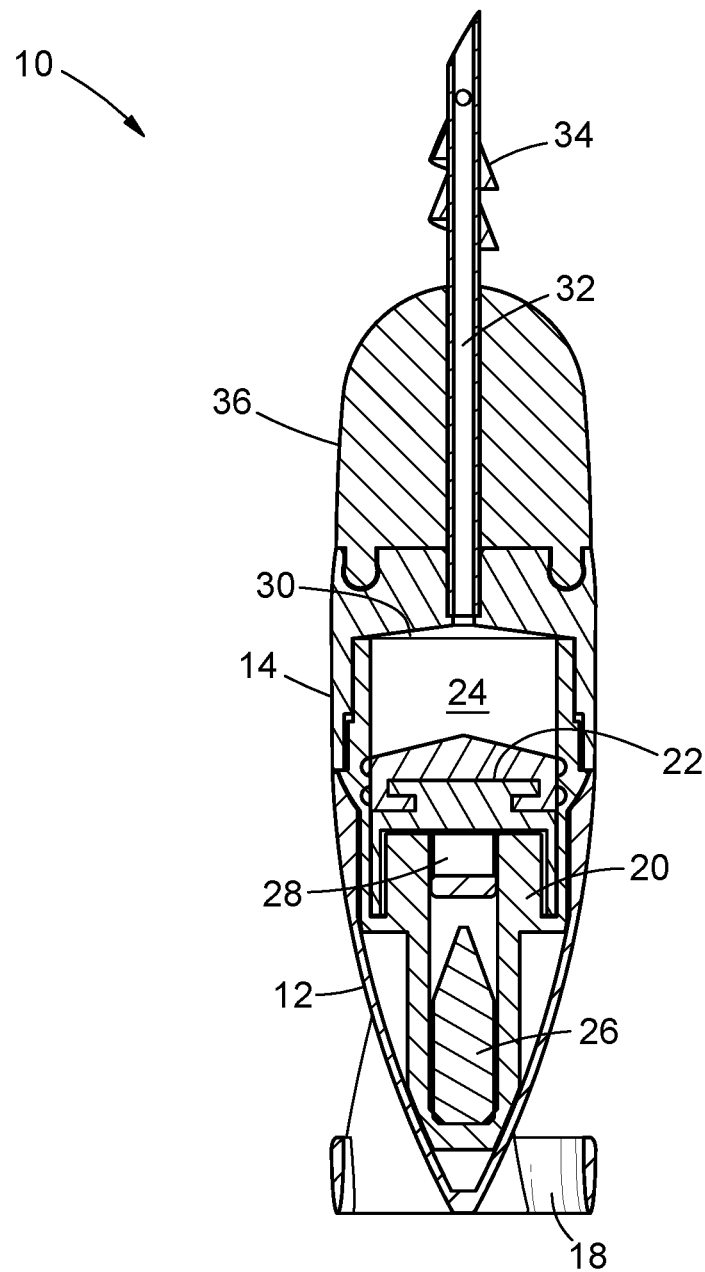
Figure 4:
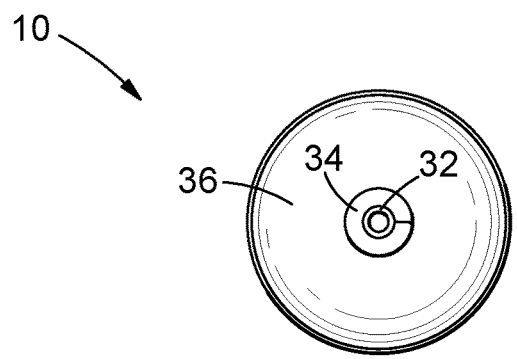
Figure 5:
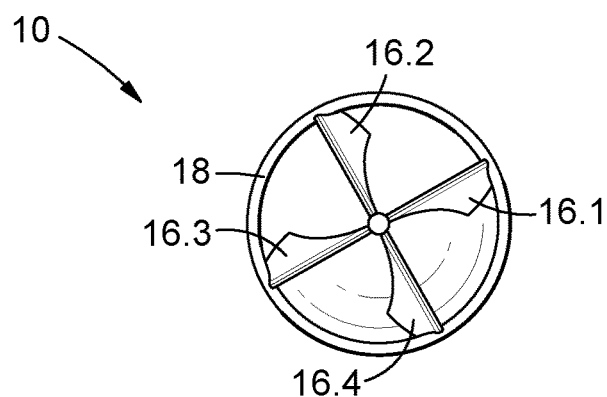

The invention is now described by way of example with reference to the accompanying drawings wherein:

FIG. 1: is a top perspective view of a dart according to an embodiment of the invention;

FIG. 2: is a side view of the dart of FIG. 1;

FIG. 3: is a cross-sectional side view of along the line III-III' of the dart of FIG. 2;

FIG. 4: is a top end view of the dart of FIG. 1;

FIG. 5: is a bottom end view of the projectile of FIG. 1; and

Figure 6:
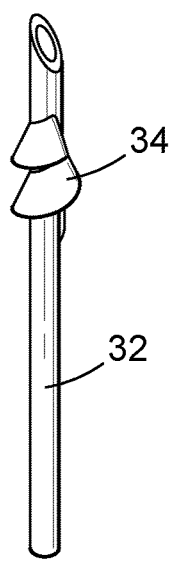

FIG. 6: is a perspective view of a dart retainer located on a hypodermic needle.

DESCRIPTION OF A PREFERRED EMBODIMENT OF THE INVENTION

Referring to the drawings, a dart in accordance with the invention is generally indicated by reference numeral 10.

Dart 10, to be fired using a paintball gun (not shown), includes a body provided as a tail 12 and extension 14; a stabilising member 16 connected to the tail 12 for stabilising the dart 10 in flight, and an annular member 18 arranged on the stabilising member 16.

The stabilising member 16 is in the form of a plurality of fins (16.1 to 16.4) in a helical arrangement relative to the tail 12, which diameter decreases towards an operative back of the dart 10 proximate to the annular member 18.

The purpose of the helically arranged fins 16.1 to 16.4 is to cause the dart 10 to spin along the longitudinal axis of the dart 10 in flight, thereby stabilizing the dart in flight and counteracting any drift due to inconsistencies in symmetry of the dart. The annular member 18 has the advantage that it ensures that the fins 16.1 to 16.4 remain in a required position, and also protects the fins 16.1 to 16.4 during packaging, handling and storage. Furthermore, the annular member 18 has substantially the same diameter and circumference as the front of the dart 10, which enables multiple darts to be stacked onto one another in a magazine (not shown), which ensures effective loading into the gun (not shown), storage of darts when not in use, and also aids in preventing the gun from jamming or misfiring. The annular member 18 also substantially increases the aerodynamic surface of the dart 10, causing the dart 10 to be fired more accurately, and to follow a more predictable and replicable flight path. The annular member 18 also moves the centre of pressure (CP) rearwards, increasing the stabilisation of the dart without increasing the frontal area of the dart. The dart 10 is configured to fit in the barrel of a paintball gun (not shown) and the diameter is configured to ensure optimum propulsion by the compressed air or other gas from the paintball gun. The annular member 18 may also include rifling lands and grooves (not shown) to facilitate operative spinning of the dart 10.

An insert 20 is located in a volume defined by the tail 12 and extension 14. A rubber plunger 22 is frictionally slidable in the insert 20 to form a chamber 24 operatively filled with an inhibitory substance (not shown), the composition of the substance being determined by the intended use of the dart 10. A striker pin 26 in the insert 20 is provided to operatively strike a primer 28 located at the operative back of the plunger 22.

The extension 14 forms a wall 30 through which a hypodermic needle 32 extends and which is in fluid communication with chamber 24 to operatively deliver the substance to an animal as will be explained in more detail below. The needle 32 furthermore has a barb body in the form of a threaded collar 34 located thereon.

The extension 14 also forms a seat for a shock absorber in the form of a soft rubber cap 36 which absorbs some of the impact between the dart 10 and target to mitigate damage to the intended target.

In use, the insert 20 and extension 14 incorporating the rubber cap 36 are fitted to the tail 12 and the volume in chamber 24 filled with the desired substance. It will be understood that the components may be secured to each other in any suitable way such as by means of a suitable adhesive or the components may be secured by friction fit.

The dart 10 is loaded into a barrel of paintball gun and the diameter of the dart 10 is configured to ensure optimum propulsion by the compressed air or other gas from the paintball gun.

Once the dart 10 hits the intended target, such as an animal, the striker pin 26 is propelled against the primer 28 which detonates and causes the plunger 22 to act on the substance in the chamber 24 to expel same through the needle 32 and enter the animal.

The barb collar 34 also pierces the skin of the animal and is accordingly also located subcutaneously. In this regard, the helices of the fins 16 and the collar 34 are orientated in the same direction to facilitate entry of the collar 34 into the animal. Therefore, the longitudinal spin of the dart 10 which is imparted by the orientation of the helical fins 16 corresponds to the orientation of the helical thread of the collar 34. Rifles and grooves (not shown) may also be provided on the annular member 18 to facilitate the longitudinal spinning of the dart 10 and is accordingly of the same orientation.

The barbed ridges of the collar 34 however prevent the needle 32 from being dislodged from the animal and will remain in the animal for some time until it is removed by a user.

Once the animal is inhibited, a user may remove the dart 10 by simply pulling on the needle 32 until the collar 34 abuts the animal's skin, impart rotational force (which is converted into linear motion by the thread of the collar 34) and withdraw the needle 32 with minimal or even no damage to the tissue and skin of the animal.

The collar 34 has the added advantage of being manufactured of a water soluble material which will dissolve in due time. In this regard, when the animal cannot be tracked and located by the user or otherwise not be retrieved from the animal, the dart 10 will fall off after the lapse of a period of time thereby ridding the animal of the dart 10.

As mentioned, the dart 10 may be used in known paintball guns and a specific and exclusive dart gun need accordingly not be obtained and used by a user.

The components are furthermore interchangeable and replaceable. The collar 34 may also be retrofitted onto existing darts.

It is accordingly asserted that the disadvantages associated with known darts could be alleviated with the dart according to the invention.

It will be appreciated that in terms of the invention, variations in details are possible without departing from the scope of the invention.

The invention claimed is:

1. A dart comprising
   a body, the body defining a chamber having a plunger and a striker pin located therein, the striker pin configured to operatively strike a primer for actuating the plunger when the dart hits an animal to operatively deliver a substance through a hypodermic needle extending through a front end of the body, and
   a retainer comprising a barb body locatable on the hypodermic needle characterised in that the barb body is threaded which prevents the dart from being dislodged from the animal until the dart is removed by a user while allowing the user to remove the dart when the animal is inhibited by imparting rotational force resulting in minimal damage to a tissue and skin of the animal.

2. The dart of claim 1, wherein the body includes a stabilising member connected to a tail of the body for stabilising the dart in flight when the dart is discharged from a weapon, and an annular member connected to the stabilising member at a rear end of the stabilising member.

3. The dart of claim 2, wherein the striker pin, the primer and the plunger are disposed in an insert.

4. The dart of claim 2, wherein the annular member is substantially a same circumference as the front end of the body.

5. The dart of claim 4, wherein a circumference of the body decreases towards the annular member.

6. The dart of claim 2, wherein the stabilising member is a plurality of fins helically arranged relative to the body to cause the dart to operatively spin along a longitudinal axis of the dart; and wherein an orientation of helices of the fins and the barb body is the same such that a direction of spin of the dart corresponds to a thread orientation of the barb body to facilitate entry of the barb body into the animal.

7. The dart of claim 1, wherein the front end of the body includes a shock absorber member.

\* \* \* \* \*